(12) United States Patent
Drobnik et al.

(10) Patent No.: US 7,988,612 B2
(45) Date of Patent: Aug. 2, 2011

(54) CARRIER-FREE $^{103}$PD BRACHYTHERAPY SEEDS

(75) Inventors: Michael Drobnik, Carol Stream, IL (US); Christopher Drobnik, Carol Stream, IL (US); Dave Bolenbaugh, Wheeling, IL (US); Pamela S. Dahl, Streamwood, IL (US); Irene Pahigianis, Skokie, IL (US); Scott Romanoff, Hoffman Estates, IL (US)

(73) Assignee: Medi-Physics, Inc., Princeton, NJ (US)

( * ) Notice: Subject to any disclaimer, the term of this patent is extended or adjusted under 35 U.S.C. 154(b) by 304 days.

(21) Appl. No.: 10/333,195

(22) PCT Filed: Jul. 16, 2001

(86) PCT No.: PCT/US01/22271
§ 371 (c)(1),
(2), (4) Date: Oct. 14, 2005

(87) PCT Pub. No.: WO02/07784
PCT Pub. Date: Jan. 31, 2002

(65) Prior Publication Data
US 2006/0052654 A1    Mar. 9, 2006

(51) Int. Cl.
*A61N 5/00*    (2006.01)
(52) U.S. Cl. .......................................................... 600/8
(58) Field of Classification Search ................ 600/1–8; 424/1.11, 1.29, 1.33, 1.37, 1.53, 1.61, 1.65, 424/1.25; 428/457, 655, 680, 686, 926, 935, 936; 427/5, 304, 305, 405, 437; 205/80, 170, 181, 188, 191, 197, 261; 604/509; 106/1.12, 1.13, 1.15, 1.18, 1.21, 1.26, 1.27; 606/7; 128/897–899
See application file for complete search history.

(56) References Cited

U.S. PATENT DOCUMENTS

| | | | | |
|---|---|---|---|---|
| 4,323,055 A * | 4/1982 | Kubiatowicz | ................ | 424/1.11 |
| 5,405,309 A * | 4/1995 | Carden, Jr. | ........................ | 600/3 |
| 6,042,937 A * | 3/2000 | Hayashi et al. | ................ | 428/323 |
| 6,066,083 A * | 5/2000 | Slater et al. | ........................ | 600/8 |
| 6,103,295 A * | 8/2000 | Chan et al. | ........................ | 427/5 |
| 6,143,431 A * | 11/2000 | Webster | ........................ | 428/669 |
| 6,163,947 A * | 12/2000 | Coniglione | ........................ | 29/458 |
| 6,264,599 B1 * | 7/2001 | Slater et al. | ........................ | 600/7 |

FOREIGN PATENT DOCUMENTS

| | | |
|---|---|---|
| EP | 1 149 592 | 10/2001 |
| WO | WO 00/28554 | 5/2000 |
| WO | WO 00/29501 | 5/2000 |
| WO | WO 01/87409 | 11/2001 |
| WO | WO 01/87418 | 11/2001 |

* cited by examiner

*Primary Examiner* — Charles A Marmor, II
*Assistant Examiner* — Christine D Hopkins
(74) *Attorney, Agent, or Firm* — Robert F. Chisholm

(57) ABSTRACT

A brachytherapy seed comprising (a) carrier-free $^{103}$Pd isotope, (b) a substrate for the carrier-free $^{103}$Pd radioisotope, and (c) a casing for encapsulating the carrier-free $^{103}$Pd-laden substrate, is disclosed.

19 Claims, 2 Drawing Sheets

CARRIER-FREE $^{103}$PD BRACHYTHERAPY SEEDS

FIELD OF THE INVENTION

The present invention relates to radiotherapy and to carrier-free palladium-103 ($^{103}$Pd) brachytherapy seeds used in therapeutic medical treatments. In particular, the present invention relates to radioactive brachytherapy seeds comprising: (a) a carrier-free $^{103}$Pd radioisotope, (b) a substrate for the carrier-free $^{103}$Pd radioisotope, and (c) a casing for encapsulating the carrier-free $^{103}$Pd-laden substrate.

BACKGROUND OF THE INVENTION

Radiation therapy is the treatment of diseases and conditions, especially the treatment of tumors, including malignant tumors, with radiation. In radiation therapy, the ultimate aim is to destroy the malignant tissue without causing excessive radiation damage to nearby healthy, and possibly vital, tissue. This is difficult to accomplish because of the proximity of malignant tissue to healthy tissue.

Medical personnel and investigators have developed methods for preferentially irradiating deep seated diseased tissue as opposed to healthy tissue. These methods include the use of high energy X-ray beams together with cross fire and rotational techniques which create a radiation pattern that is maximized at the site of the diseased tissue. Nonetheless, some absorption and damage inevitably occurs to healthy tissue in the path through which radiation passes to arrive at deep-seated diseased tissue.

One method of limiting the zone of irradiation utilizes radioactive articles in the form of small, radioactive "seeds," which are permanently or temporarily implanted at the zone to be irradiated. Such seeds contain a radioactive source disposed within a sealed capsule. The small size of the therapeutic seeds allows the seeds to be inserted or implanted within or near the tissue to be treated, for example, to totally surround the treated tissue.

Radiation treatment can involve a temporary implantation of a radioactive source for a calculated period, followed by its removal. Alternatively, the radioactive source can be implanted in the patient permanently and left to decay to an inert state over a predictable time. The use of temporary or permanent implantation depends on the disease or condition being treated, the radioisotope selected, and the duration and intensity of required treatment.

The advantages of interstitial implantation of a radiation-emitting article for localized tumor treatment have long been recognized. Interstitially implanted articles concentrate the radiation at a zone where radiation treatment is needed, e.g. near or within diseased tissue in order to directly affect diseased tissue, while exposing normal, healthy tissue to substantially less radiation than beaming radiation into the body from an external source.

Implanting radioactive articles in proximity to or directly within diseased or damaged tissue within a body is a therapy referred to as brachytherapy (i.e. short-range therapy). Brachytherapy is a general term for a medical treatment involving placement of a radioactive source near diseased tissue. Brachytherapy has been proposed for use in the treatment of a variety of diseases and conditions, including arthritis and cancer, for example, breast, brain, liver, and ovarian cancer, and especially prostate cancer in men [see for example, J. C. Blasko et al., The Urological Clinics of North America, 23, 633-650 (1996), and H. Ragde et al., Cancer, 80, 442-453 (1977)]. This form of therapy permits the application of larger doses of radiation directly to diseased or damaged tissue, like tumors.

Permanent implants for prostate cancer treatment comprise radioisotopes with relatively short half-lives and lower energies relative to radioisotopes used in temporary implants. Examples of permanently implantable radioisotopes include iodine-125 and palladium-103. The radioisotope generally is disposed on a substrate, which is encapsulated in a metal casing, for example, a titanium casing, to form a "seed," which is then implanted in the patient.

Radioactive seeds are disclosed, for example, in Lawrence U.S. Pat. No. 3,351,049 and Kubiatowicz U.S. Pat. No. 4,323,055. U.S. Pat. No. 3,351,049 discloses conventional brachytherapy seeds comprising titanium containers encapsulating ion exchange resin beads onto which a radioactive ion, e.g. $^{125}$I or $^{103}$Pd has been adsorbed. U.S. Pat. No. 3,351,049 also discloses that $^{103}$Pd, preferably carrier-free, could be plated on a 3.5 mm long plastic rod. However, U.S. Pat. No. 3,351,049 does not disclose any method of plating carrier-free $^{103}$Pd onto the plastic rod. As discussed hereafter, the uniform distribution of carrier-free $^{103}$Pd on a substrate has been an ongoing and unsolved problem. U.S. Pat. No. 4,323,055 discloses brachytherapy seeds comprising a coating of radioactive silver iodide on a silver wire encapsulated inside a titanium container. WO 97/19706 discloses the immobilization of a radioactive powder within a polymeric matrix.

The seeds disclosed in prior patents comprise a tiny sealed capsule having an elongate cavity containing the radioisotope, e.g., iodine-125 ($^{125}$I) or palladium-103 ($^{103}$Pd), adsorbed onto a substrate. Such seeds are suitable for use with radioisotopes that emit radiation capable of penetrating the capsule walls. Therefore, the seeds generally contain radioisotopes that emit γ-radiation or low-energy X-rays, as opposed to β-emitting radioisotopes. Because of the low energy X-rays emitted by $^{125}$I and $^{103}$Pd, and the short half-life of $^{125}$I and $^{103}$Pd, the seeds can remain implanted in the tissue of a patient indefinitely without excessive damage to surrounding healthy tissue or excessive exposure to other individuals near the patient.

In order to function effectively, radiation emitting from the radioisotope within the seed should not be blocked or otherwise unduly attenuated. Seeds based on metal wire substrates have the disadvantage that a portion of the radioactivity is absorbed by the wire substrate itself, i.e. the radioactive emissions from the seed are attenuated by the wire. The amount of radioactivity absorbed by the wire increases as the atomic number (i.e. Z) of the metal wire substrate increases. The precise amount of attenuation is related to the identity and the dimensions of the wire substrate. For example, silver iodide-125 coated on an 0.5 mm diameter silver wire has up to about 40-50% of the radioactivity absorbed by the silver wire. Therefore, in the manufacture of a radioactive seed of a preselected activity, additional $^{125}$I is loaded onto the wire to account for the absorption of radioactivity by the wire and also by the seed capsule. As the preselected radioactivity of the seed increases, the cost of the extra amount of radioisotope which is loaded onto the wire substrate also increases.

Radiation emitted from the radioisotope also should be distributed uniformly from the seed in all directions, i.e. an isotropic radial distribution. Providing a uniform distribution of radiation from a seed has been difficult to accomplish. For example, present-day seeds have a radioisotope adsorbed onto a carrier substrate, which is placed into a metal casing that is welded at the ends. The most advantageous materials of construction for the casing which encapsulates the radioisotope-laden carrier are stainless steel, titanium, and other low atomic number metals, with titanium and titanium alloys being preferred. However, problems exist with respect to sealing casings made from these materials.

In particular, metallic casings typically are sealed by welding, but welding of such small casings is difficult because welding can locally increase the casing wall thickness, or can introduce higher atomic number materials at the ends of the casing where the welds are located. The presence of such localized anomalies can significantly alter the geometrical configuration at the welded ends, resulting in undesirable shadow effects in the radiation pattern emanating from the seed. Such seeds also have the disadvantage of providing a non-homogeneous radiation dose to the target due to their construction, i.e. the relatively thick ends attenuate the emanating radiation more than the relatively thin body of the seed.

Problems also have been encountered in homogeneously applying the radioisotope to the substrate. Brachytherapy seeds are small in size, and the amount of radioisotope present in each seed is extremely small, e.g. less than $1 \times 10^{-6}$ g of radioactive isotope per seed. The amount of radioisotope present in each seed necessarily decreases as the specific activity of the isotope increases. This presents severe handling and manufacturing problems with respect to homogeneously applying a small chemical amount of radioisotope onto the substrate, especially when the radioisotope is carrier-free. These problems, together with safety problems, increase in scope as the radioactivity of the isotope increases.

Several patents are directed to implantable radioactive seeds for use in brachytherapy. Examples of such patents include Kubiatowicz U.S. Pat. No. 4,323,055; Suthanthiran U.S. Pat. No. 4,891,165; Russell, Jr. et al. U.S. Pat. Nos. 4,784,116 and 4,702,228; Lawrence U.S. Pat. No. 3,351,049; Good U.S. Pat. No. 5,342,283; Carden, Jr. U.S. Pat. No. 5,405,309; and Langton et al. U.S. Pat. No. 5,460,592.

U.S. Pat. No. 5,405,309 addresses the previously mentioned problem of uniformly distributing carrier-free $^{103}$Pd on a substrate. The specific problem addressed by U.S. Pat. No. 5,405,309 is that carrier-free radioisotopes are present in a seed at vanishingly small amounts, and that use of an extremely dilute carrier-free radioisotope solution presents significant handling problems, in addition to safety problems associated with an intensely radioactive composition. U.S. Pat. No. 5,405,309 teaches that $^{103}$Pd can be applied more easily, evenly, and safely to a substrate by admixing non-radioactive palladium metal (i.e. carrier Pd) with carrier-free $^{103}$Pd to increase the physical mass of the palladium and facilitate application of the palladium onto the substrate.

Because $^{103}$Pd is expensive to produce, it is important that application of the $^{103}$Pd radioisotope onto the substrate is as efficient and reproducible as possible. The method of U.S. Pat. No. 5,405,309 utilizes electroplating, i.e. a process involving passage of an electric current, to achieve a homogeneous distribution of $^{103}$Pd on the substrate. However, the addition of non-radioactive palladium metal, i.e. carrier Pd, to facilitate electroplating of $^{103}$Pd attenuates the low energy X-ray emissions of the $^{103}$Pd adsorbed onto the substrate by providing an additional high Z material that attenuates radiation emanating from radioactive $^{103}$Pd. The result is that additional $^{103}$Pd must be applied to the substrate to attain at least a threshold radioactive dose. This adds to the cost of such $^{103}$Pd seeds. It is a major disadvantage to prepare costly carrier-free $^{103}$Pd (eg. using a high energy cyclotron), then to use a process that provides a product wherein a portion of the radioactive emissions are effectively lost by dilution of carrier-free $^{103}$Pd with carrier Pd.

Although the above patents illustrate improvements in seeds for use in brachytherapy, the art still suffers from the problem of providing a $^{103}$Pd seed that, simultaneously, is easy to manufacture and has a uniform distribution of radioisotope on the substrate, while minimizing attenuation of radioactivity emanating from the seed. The present invention is directed to providing $^{103}$Pd brachytherapy seeds having these attributes.

SUMMARY OF THE INVENTION

The present invention is directed to $^{103}$Pd-containing brachytherapy seeds. More particularly, the present invention is directed to carrier-free $^{103}$Pd brachytherapy seeds, wherein the carrier-free $^{103}$Pd is homogeneously deposited on a substrate to provide a uniform radiation dose in the treatment of a disease, like cancer.

Accordingly, one aspect of the present invention is to provide brachytherapy seeds comprising carrier-free $^{103}$Pd adsorbed on the surface of a suitable substrate. Preferably, the seed has a total activity of about 10 to 75 MBq (ca. 0.3 to 2 mCi), preferably 25 to 50 MBq (ca. 0.7 to 1.4 mCi), and more preferably 30 to 45 MBq (ca. 0.8 to 1.2 mCi).

Another aspect of the present invention is to provide a method of manufacturing a brachytherapy seed comprising carrier-free $^{103}$Pd adsorbed onto a substrate. The method comprises an electroless deposition of carrier-free $^{103}$Pd onto a substrate.

Yet another aspect of the present invention is to provide a substrate for a carrier-free $^{103}$Pd brachytherapy seed, wherein, in one embodiment, the substrate comprises a core of a radiopaque metal (e.g. silver), a sheath of a radiotransparent metal (e.g. aluminium) surrounding the core, and a coating of a material suitable for an electroless deposition of $^{103}$Pd (e.g. copper or nickel) applied over the radiotransparent metal sheath. In a preferred embodiment, the outer metal coating comprises nickel.

In another embodiment, the core of the substrate comprises a radiotransparent core, such as a polymer, graphite, or a low atomic number (Z) metal, such as aluminium. The radiotransparent core is coated with a material suitable for an electroless deposition of $^{103}$Pd.

These and other aspects of the invention will become apparent from the following detailed description of the preferred embodiments, taken in conjunction with the Figures.

DETAILED DESCRIPTION OF THE PREFERRED EMBODIMENTS

Figure 1:
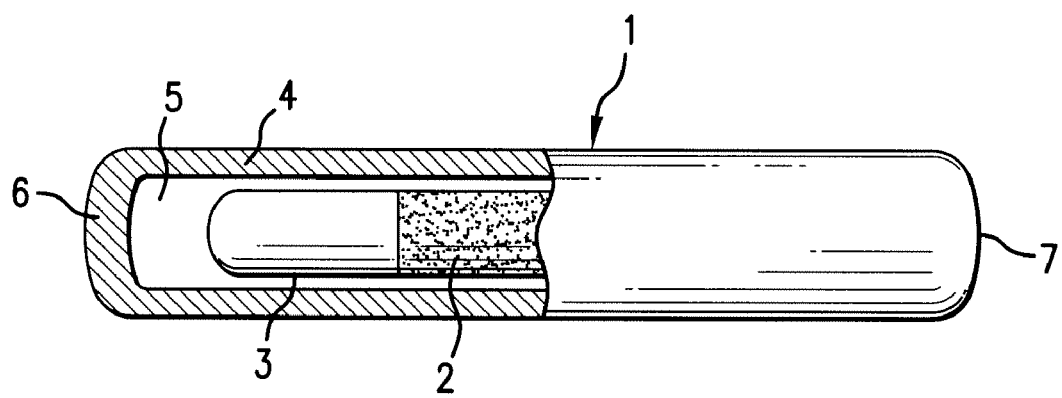
FIG. 1 is a partially cut-away side view of a present brachytherapy seed.

Brachytherapy is a form of radiation therapy wherein a radioactive source is positioned near, or within, a radiation target, e.g. a tumor. The radioactive source is delivered in the form of a seed containing a radioisotope that has been applied to a substrate. The radioisotope-laden carrier is encapsulated by, and sealed within, a suitable metal casing.

Various radioisotopes have been used in brachytherapy, and several factors are considered when deciding which radioisotope is used for a particular therapy. These factors include the type and intensity of radiation emanating from the radioisotope, the half-life of the radioisotope, and the particular disease or condition being treated. The decision also encompasses considerations of efficacy of the therapy, safety to surrounding healthy tissue, and safety to medical personnel that handle and implant the brachytherapy seeds.

The threshold radiation dose required to treat a particular disease, such as a cancer, is an important parameter in designing a brachytherapy seed. A threshold dosage must reach the target site for effective treatment, but a significant percentage of the radiation emitted from a brachytherapy seed is attenuated and unavailable for therapeutic purposes. For example, the substrate absorbs a significant portion of the emitted radiation, and the casing further attenuates radiation emanating from the seed. In addition, prior seed designs can suffer in having the radioisotope unevenly distributed on the substrate. This results in an uneven radiation dose emanating from the seed as a whole. Accordingly, the amount of radioisotope applied to the carrier is increased such that the seed as a whole emits at least the threshold radiation dose necessary to treat the disease.

It would be desirable, therefore, to provide a brachytherapy seed wherein attenuation of radiation emanating from the radioisotope is reduced. Reducing the amount of attenuation, while maintaining the threshold radiation dose to treat the disease, has several advantages, including a reduced gross amount of radioisotope applied to the substrate, an increased safety to personnel that manufacture, handle, and implant the seeds, and a significant cost savings.

In a first aspect, the present invention provides:
a brachytherapy seed which comprises:
(a) a substrate having a surface suitable for the electroless deposition of palladium,
(b) carrier-free $^{103}$Pd disposed on said surface of said substrate to provide a carrier-free $^{103}$Pd-laden substrate; and
(c) a biocompatible casing for encapsulating the carrier-free $^{103}$Pd-laden substrate.

The present invention, therefore, is directed to carrier-free $^{103}$Pd seeds, i.e. seeds free of non-radioactive palladium and other metals, and methods of manufacturing such seeds. As used herein, "carrier-free $^{103}$Pd" is defined as palladium-103 which does not include non-radioactive palladium metal or other palladium isotopes added, or other non-radioactive metals, as a carrier. The present process utilizes electroless plating of carrier-free $^{103}$Pd onto a substrate. By the term "electroless" is meant a process that does not utilize the passage of an electric current. As a result, seed manufacture is simplified, and no additional carrier is present to attenuate $^{103}$Pd emissions.

The present invention provides a simple and efficient method of depositing carrier-free $^{103}$Pd onto a suitable substrate, which in turn is loaded into a seed casing. A preferred method utilizes electroless deposition of carrier-free $^{103}$Pd onto a surface of a "wire" or "pin" (i.e. a short metallic rod) substrate.

By the term "surface suitable for the electroless deposition of palladium" is meant a surface material which, on contact with palladium ions in solution, in the presence of a reducing agent, reacts to deposit palladium metal on the surface in an autocatalytic chemical reduction. In particular, carrier-free $^{103}$Pd is deposited on a catalytic substrate surface from a solution containing $^{103}$Pd and a reducing agent. Preferred such surface materials suitable for the electroless deposition of palladium are nickel, copper or mixtures thereof. Nickel is especially preferred.

Suitably, the substrate is a cylindrical rod or wire having a treated surface to which the carrier-free $^{103}$Pd is applied. The substrate serves primarily as a solid support on which the carrier-free $^{103}$Pd is uniformly distributed. A substrate utilized in the present invention can be constructed of any material that serves as a solid support for the carrier-free $^{103}$Pd. It is preferred that the substrate is constructed from a material that is detectable by X-rays, i.e. is radiopaque, to serve as an X-ray marker. This enables medical personnel to properly position the seeds near or in the target site, and to scan the patient at a later date to determine whether the seeds have moved from the target site.

The substrate, therefore, is constructed from any material onto which the requisite therapeutic amount of carrier-free $^{103}$Pd can be attached, and preferably, that is detectable by X-rays or other detection means. Silver and copper are preferred materials for the substrate, because these metals provide good X-ray visualization. Also, carrier-free $^{103}$Pd also can be easily attached to a copper surface. Other X-ray opaque metals, such as gold and iron, for example, can be used as a substrate. The substrate also can be a radiotransparent metal, or non-metallic material such as a polymer or graphite rod, that is capable of having carrier-free $^{103}$Pd deposited thereon by an electroless method. When the substrate comprises a radiopaque metal, such substrates have the advantage that they function both as a carrier for the radioisotope and as a marker for detection of the seeds.

Furthermore, because the substrate generally conforms to the shape of the casing, the exact location and orientation of the seed in the tissue can be determined from X-ray photographs, for example. Preferred substrates include (a) a simple radiopaque metal rod or (b) a radiotransparent metal, polymer, or graphite rod. Suitable and preferred substrates are described in detail below.

The substrates of the present invention are generally acicular in shape, and have a circular cross section. They are of a suitable length and diameter for easy disposition into a seed casing, and preferably occupy a substantial portion of the casing cavity. The substrate preferably is about 3 mm long and 0.5 mm in diameter (maximum) when used in a standard casing having a length of 4.5 mm and an exterior diameter of 0.8 mm. A 3 mm long substrate results in minimum shifting within the casing while allowing adequate room to weld the ends of the casing without adversely affecting the substrate. The diameter of the substrate is about 0.1 mm to about 0.7 mm (the maximum inside diameter of a conventional casing). The preferred diameter is about 0.5 mm, which, if needed, provides good X-ray visibility, is relatively easy to handle during seed manufacture, and slides easily into the seed casing without abrading against the interior walls of the casing. The substrate also can be spherical in shape.

The brachytherapy seed of the present invention uniformly emits radiation over its entire geometry because of a homogeneous distribution of carrier-free $^{103}$Pd on the substrate. A uniform radiation emission from the seed reduces the amount of radioisotope needed to provide a therapeutic dose because the seed does not have any relatively "cold" spots attributed to an uneven distribution of $^{103}$Pd on the substrate. Hence, the seed does not require as large an excess of carrier-free $^{103}$Pd to provide a threshold radioactive dose, and the seed as a whole provides a therapeutic radioactive dose to the target. Prior $^{103}$Pd seeds utilized non-radioactive, carrier palladium to dilute the $^{103}$Pd, which permitted a uniform distribution of $^{103}$Pd on the substrate. For example, see U.S. Pat. No. 5,405, 309 which adds carrier Pd to carrier-free $^{103}$Pd, and U.S. Pat. No. 4,702,228 which utilizes $^{103}$Pd-enriched palladium that also contains non-radioactive Pd carrier. In contrast, the present invention utilizes carrier-free $^{103}$Pd.

The carrier-free $^{103}$Pd-laden substrates of the present invention may be prepared by an electroless deposition process. Electroless deposition of metals, including palladium, is disclosed, for example, in Heugh et al. U.S. Pat. No. 4,255,194; Abys U.S. Pat. No. 4,424,421; Josso et al. U.S. Pat. No. 5,085,693; Das et al. US 5,264,288; and Feldstein et al. U.S. Pat. No. 5,420,477, each incorporated herein by reference. The present invention shows that carrier-free $^{103}$Pd can be deposited onto a substrate to provide a seed product having an apparent activity of about 37 MBq (1 mCi) $^{103}$Pd. The carrier-free $^{103}$Pd can be deposited by an electroless method using either (a) an acid electroless plating solution containing carrier-free $^{103}$Pd in 0.1 to 0.001 N HCl, (b) an alkaline electroless plating solution containing carrier-free $^{103}$Pd, ammonium sulfate (13.2 g/L), ammonium citrate (24.3 g/L), and ammonium hydroxide (50 mL/L).

After deposition, the carrier-free $^{103}$Pd-laden substrate is sealed within a biocompatible casing. By the term "biocompatible" is meant a material that does not corrode when in contact with body fluids, and is non-toxic when implanted in the patient's body.

A brachytherapy seed casing typically is manufactured from a cylindrical tube of a metal that provides adequate thin wall strength, and that readily allows radiation to pass uniformly through the material. The thin walls permit a larger substrate to be disposed in the seed, and reduces attenuation of emitted radiation. Suitable casing materials are metals, and typically low atomic numbered metals, such as stainless steel alloy, titanium, or titanium alloy. Higher atomic number metals, such as gold or platinum, attenuate too much radiation emanating from the carrier-free $^{103}$Pd-laden substrate to be useful per se. However, higher atomic numbered metals are useful as a plating over various low atomic number materials, such as beryllium, which otherwise is too toxic if used without an outer biocompatible coating. Other suitable casing materials include, but are not limited to, tantalum, nickel alloys, copper alloys, and aluminium alloys. If the seed is designed for detection by ultrasound, as opposed to X-rays, the casing can be manufactured from an echogenic material, e.g. the casing can be predominantly aluminium. Suitable casing materials also include inert synthetic materials, for example, Teflon™. The casing is completely sealed so there is no danger of leakage.

Titanium, which has a low atomic number and a high strength-to-weight ratio, is the preferred casing material. Titanium is exceptionally corrosion-resistant, and is satisfactory from the standpoint of biocompatibility. Preferably, the titanium is a pure alloy to assure good working properties. The wall thickness of a titanium casing can be about 0.025 to about 0.127 mm, with radiation attenuation being about 7% per 0.025 mm. An optimum wall thickness for a titanium casing is about 0.051 mm. Examples of casing designs are illustrated in FIGS. 1 and 2.

A single casing can contain one radiolabeled substrate that occupies substantially all of the cavity inside the casing. Alternatively, each casing can contain two or more such substrates, for example, optionally separated by a suitable spacer. The substrate arrangement is such that there is a uniform radiation field emanating from the seed.

An example of a present brachytherapy seed is illustrated in FIG. 1, wherein a seed [1] contains a therapeutic amount of carrier-free $^{103}$Pd [2] disposed on a substrate [3]. The carrier-free $^{103}$Pd-laden substrate [3] is disposed in a cavity [5] of a cylindrical casing [4]. Casing [4] is sealed at ends [6] and [7], typically by welding. FIG. 2 illustrates another embodiment of a present brachytherapy seed [10] having a carrier-free $^{103}$Pd-laden substrate [12] encapsulated by a casing [14]. Casing [14] is a tube having a centre portion [16] and two end portions [18]. Centre portion [16] has a diameter [$d_1$] that is substantially larger than the diameter [$d_2$] of end portions [18]. Ends [20] and [22] are sealed, for example by plasma discharge welding.

Figure 2:
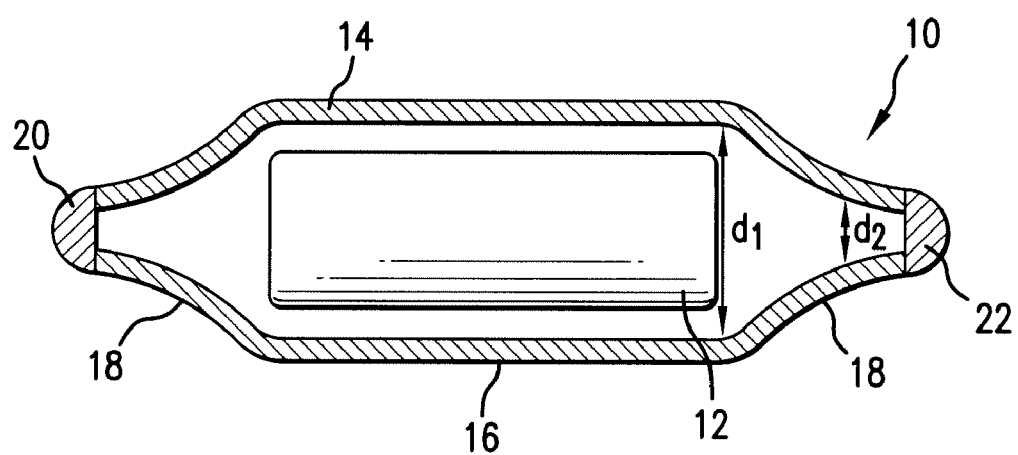
FIG. 2 is a cut-away side view of another embodiment of a present brachytherapy seed.

In FIG. 2, a cylindrical tube, such as a titanium tube, of uniform diameter is swaged at each end to provide a tube having a centre portion of a first diameter and end portions of a second diameter, wherein the second diameter is substantially less than the first diameter. In particular, the diameter of each end portion of the swaged tube, independently, is about 25% to about 80% less than the diameter of the center portion of the tube. The casing ends are sealed by standard techniques such as plasma discharge, laser, electron beam, or tungsten inert gas (TIG) welding.

The overall size of a brachytherapy seed casing is designed for implantation by perforate penetration or injection, e.g. by hypodermic needle or similar device especially designed for positioning brachytherapy seeds. Therefore, the casing has a relatively narrow maximum outer diameter of about 0.25 to about 1 mm, and about 0.25 to about 25 mm in length. For permanent implantation, as by hypodermic injection, the outside diameter of the seed is preferably about 0.80 mm and is small enough to pass through a 17-gauge hypodermic needle. The seed typically is about 4 to 5 mm long. Such seeds exhibit minimal movement in the tissue and do not migrate from the area where they are implanted.

Carrier-free $^{103}$Pd is produced by a high current cyclotron bombardment of a rhodium target at an energy of about 15 to about 20, and typically about 18 MeV (mega electron volts). $^{103}$Pd produced in a cyclotron is carrier-free, unlike nuclear reactor-produced $^{103}$Pd. $^{103}$Pd produced in a nuclear reactor results from the bombardment of $^{102}$Pd. The abundance of $^{102}$Pd is 1.0% of naturally-occurring palladium. The most enriched $^{102}$Pd which can be used in the $^{103}$Pd reactor process contains about 75-80% $^{102}$Pd with the remaining 20-25% being other Pd and non-Pd isotopes. The maximum specific activity of $^{103}$Pd produced in a nuclear reactor is about 12,950 GBq/g (ca. 350 Ci/g). In contrast, carrier-free $^{103}$Pd produced in a cyclotron has a specific activity of about 2,775,000 GBq/g (ca. 75,000 Ci/g).

The term "specific activity" as used herein means the total activity of $^{103}$Pd per gram of material. The term "therapeutic or apparent activity" as used herein means the $^{103}$Pd activity as determined from measuring the X-ray intensity outside the seed. This is the therapeutic activity that treats the disease or condition, and, therefore the activity used when developing a treatment plan for a patient.

It can be seen that utilizing carrier-free $^{103}$Pd as the radioisotope can greatly reduce the gross amount of Pd adsorbed onto the substrate because of the extremely high specific activity of carrier-free $^{103}$Pd. By adsorbing only carrier-free $^{103}$Pd onto a substrate, attenuation of $^{103}$Pd emissions is reduced because non-radioactive carrier Pd is not present on the substrate. In addition, the step of adding carrier Pd to carrier-free $^{103}$Pd is eliminated, thereby eliminating one manipulation step involving a very highly radioactive material.

Carrier-free $^{103}$Pd can be prepared, for example, by depositing rhodium metal onto a suitable substrate, such as a copper or a silver substrate. The resulting rhodium target is then placed in a charged particle accelerator, such as a cyclotron, and bombarded with protons or deuterons. The energy of the impacting particle, i.e. about 18 MeV, is selected such that essentially the only Pd atoms created on the rhodium target are $^{103}$Pd, that is, the $^{103}$Pd is carrier-free.

The rhodium metal target containing the carrier-free $^{103}$Pd is then treated to remove the rhodium metal from the substrate, for example, by etching with an acid, such as nitric acid (HNO$_3$). This removal step often is accomplished by mechanically disrupting the continuity of the rhodium layer on the substrate, for example, by perforating the rhodium surface with a sharply pointed tool. The exposed (i.e. non deposit-containing) substrate surface is protected by an inert covering layer and the perforated target is immersed in an HNO$_3$ bath. A mixture containing rhodium flakes results, which is filtered to recover the solid rhodium flakes containing $^{103}$Pd. The recovered rhodium flakes are rinsed on the filter, and the flakes together with the filter are placed in a crucible and heated to decompose the filter and leave the rhodium metal flakes containing the $^{103}$Pd.

The rhodium metal flakes are then partially dissolved in molten NaHSO$_4$ (sodium bisulfate), and the resulting NaHSO$_4$/rhodium flake mixture is dissolved in dilute hydrochloric acid (HCl). This procedure is repeated several times in order to dissolve any remaining rhodium metal containing carrier-free $^{103}$Pd.

This method of producing carrier-free $^{103}$Pd is fully disclosed in Carden, Jr., U.S. Pat. No. 5,405,309, incorporated herein by reference.

Alternatively, carrier-free $^{103}$Pd can be produced by the high current cyclotron bombardment of a natural rhodium target with protons at an energy of approximately 18 MeV. The rhodium cyclotron target is produced by electroplating natural rhodium onto a copper support. Following bombardment, the rhodium-electroplated region of the copper support is removed from the bulk of the copper support, i.e. the rhodium-electroplated region is punched out from the support. The rhodium region then is placed in a 50% nitric acid solution to remove the remaining copper backing. The rhodium metal next is dissolved in concentrated hydrochloric acid. Hydrogen tetrachloroaurate trihydrate can be added (e.g. at 2 to 3 times the weight of rhodium, preferably the stoichiometric amount of rhodium) to speed dissolution. In addition, dissolution can be facilitated by heating the hydrochloric acid solution, and applying an alternating current with graphite electrodes.

The resulting solution contains rhodium metal, rhodium isotopes, and $^{103}$Pd in approximately 6N hydrochloric acid. The solution is transferred to an extractor, and an organic compound, e.g. 0.25% α-furyldioxime in 20% aqueous ethanol, then is added to produce an organic-soluble $^{103}$Pd metal complex. This complex is extracted with chloroform (3×50 ml). The combined chloroform extracts are washed with dilute hydrochloric acid, then the chloroform is evaporated to dryness. The residue is treated with a mixture of aqua regia (4:1 HCl:HNO$_3$) and 30% hydrogen peroxide to decompose any remaining organic materials. The remaining carrier-free $^{103}$Pd then is solubilized in dilute hydrochloric acid.

Figure 3:
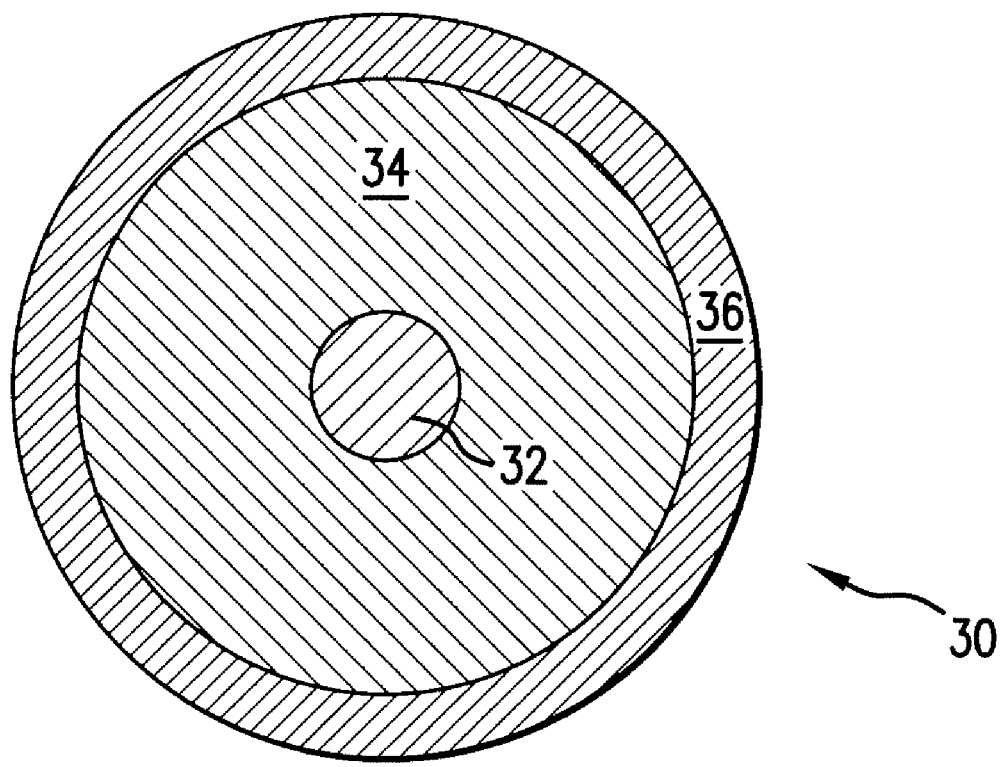
FIG. 3 is a cross-sectional view of one embodiment of a substrate for a present brachytherapy seed.

In a second aspect, the present invention provides a substrate in a form suitable for use in a brachytherapy seed, which has a surface coating suitable for the electroless deposition of palladium and further comprises a radiopaque metal core chosen from silver, platinum, iridium, palladium, thallium, copper, iron or lead or a mixture thereof, surrounded by a sheath of a radiotransparent metal. In one preferred embodiment, the substrate has concentric zones comprising the radiopaque metal core/a radiotransparent metal sheath/a coating suitable for electroless deposition of palladium, (eg. carrier-free $^{103}$Pd), as illustrated in FIG. 3 and described in detail hereafter. For such a concentric substrate, a preferred radiotransparent metal sheath comprises aluminium, and a preferred radiopaque core material is silver.

One preferred substrate is illustrated in FIG. 3. In FIG. 3, substrate [30] comprises a radiopaque metal core [32] surrounded by a radiotransparent metal sheath [34]. The radiotransparent metal sheath [34] is covered by a coating [36] of a material suitable for an electroless deposition of carrier-free $^{103}$Pd, for example, a metal like copper or nickel.

The core [32] is preferably radiopaque to X-rays and therefore useful for imaging implanted seeds, because the casing and metal sheath [34] are relatively transparent to X-rays. Sheath [34] comprises a low atomic number material, like aluminium, to further minimize attenuation of the carrier-free $^{103}$Pd emissions. The metal coating [36] has electrochemical properties that facilitate electroless deposition of carrier-free $^{103}$Pd onto the substrate. The electroless $^{103}$Pd plating is performed using carrier-free $^{103}$Pd in aqueous acid or base solution, preferably in the presence of a buffer and/or a reducing agent, e.g. hydrazine.

Substrate [30] typically has a length of about 2.5 to about 5 mm. The outer diameter of substrate [30] is about 0.25 to about 0.8 mm, typically about 0.5 mm. Core [32] has a diameter of about 0.05 mm to about 0.3 mm, and metal sheath [36] has a thickness of about 0.1 to about 0.3 mm.

A radiopaque core [32] comprises a metal having a high Z, for example silver, gold, platinum, iridium, palladium, thallium, copper, iron, or lead. Radiotransparent sheath [34] comprises a low Z metal, like aluminium. The presence of a low Z metal in sheath [34] reduces attenuation of radiation emitted from the carrier-free $^{103}$Pd. A radiotransparent core, either free of or having a radiotransparent sheath, also reduces attenuation of radiation emitted by the carrier-free $^{103}$Pd.

In most preferred embodiments, substrate [30] is coated with a thin coating [36] of a material suitable for an electroless deposition of $^{103}$Pd, such as a metal like nickel or copper, about $2 \times 10^{-3}$ to about $5 \times 10^{-3}$ mm thick. Coating [36] facilitates electroless coating of carrier-free $^{103}$Pd onto substrate [30]. In most preferred embodiments, coating [36] comprises nickel.

In a third aspect, the present invention provides a substrate in a form suitable for use in a brachytherapy seed, which comprises a radiotransparent core with a surface coating, wherein the surface coating is suitable for the electroless deposition of palladium. The radiotransparent core may suitably comprise: a polymer, graphite, or a low Z metal, having a coating of a material suitable for electroless deposition of $^{103}$Pd.

Substrates of this type are particularly useful when means other than X-ray visualisation are utilized to detect and position the seeds near or in a target site, because a radiopaque core is no longer essential. For example, if the seeds are detected using ultrasound, and the material of construction of the casing is echogenic, then the substrate can be radiotransparent. Alternatively, substrates of this type may be chosen such that the thickness of the metallic coating on the radiotransparent core exceeds about 0.05 mm, so that the coating itself ensures X-ray visualisation.

Such substrates can be prepared by depositing a suitable metal (chemically or by using "sputtering" and "ion plating" techniques) onto a substrate other than a metal, e.g. a polypropylene filament.

In a fourth aspect, the present invention provides a method of preparing a carrier-free $^{103}$Pd-laden substrate which comprises: immersing a substrate having a surface suitable for the electroless deposition of palladium into an electroless bath comprising carrier-free $^{103}$Pd for a sufficient time to deposit a pre-selected amount of carrier-free $^{103}$Pd onto the surface suitable for the electroless deposition of palladium of said substrate. The surface suitable for the electroless deposition of palladium preferably comprises nickel or copper or a mixture thereof. The electroless bath comprises either (a) an acid electroless plating solution containing carrier-free $^{103}$Pd in 0.1 to 0.001 N HCl, (b) an alkaline electroless plating solution containing carrier-free $^{103}$Pd, ammonium sulfate (13.2 g/L), ammonium citrate (24.3 g/L), and ammonium hydroxide (50 mL/L).

In a further aspect, the carrier-free $^{103}$Pd seeds of the present invention can be used to treat conditions responsive to brachytherapy. Such conditions include: head and neck cancers, melanoma, brain cancers, non-small cell lung cancer, breast cancer, and ovarian, uterine, and cervical cancer, and other diseases including proliferative diseases, arthritis, urethral stricture, and fibroid uterine tumors.

The present carrier-free $^{103}$Pd seeds can thus be used in a method of treating a disease or condition that is responsive to radiation therapy, for example, a cancer, which comprises the permanent or temporary placement of a seed comprising an amount of carrier-free $^{103}$Pd adsorbed on the surface of a suitable substrate, at the site to be treated within a patient for a sufficient period of time to deliver a therapeutically effective dose.

The therapeutically effective dose can be easily determined by persons skilled in the art based on the condition or disease that is being treated, the severity of the disease or condition, the individual patient, and the strength of the radiation emanating from the carrier-free $^{103}$Pd seeds.

The amount of carrier-free $^{103}$Pd required to provide a therapeutically effective dose depends in part on the amount of radiation absorbed by the substrate and by the casing. The amount of attenuation in any given case can be readily determined by a skilled person, for example, by trial-and-error experimentation or by calculation, and the amount of carrier-free $^{103}$Pd adsorbed onto the carrier can be adjusted accordingly. For example, the ratio of the specific activity of the substrate to the apparent activity of the seeds may be about 1.5 to about 2 to 1, due to absorption by a silver substrate and a titanium casing.

EXAMPLES

The invention is illustrated by the following Examples. Example 1 shows how a coating suitable for the electroless deposition of palladium (in this case nickel), can be deposited onto a substrate. Example 2 shows the ability of an electroless method to deposit non-radioactive palladium onto a metal substrate. The electroless plating of non-radioactive palladium from dilute acid onto a copper substrate was accomplished in less than one hour. In addition, the Pd remained adhered to the copper substrate after a 24-hour soak in distilled water. Similar tests using an aluminium substrate indicated that the addition of a reducing agent to the bath facilitated Pd deposition. Example 3 shows the electroless deposition of carrier-free $^{103}$Pd onto a substrate.

Example 1

Coating of a Substrate with Nickel

A substrate can be coated with nickel by immersing the substrate in an electroless bath containing 4.7 g/L nickel sulfate hexahydrate, 3.0 g/L sodium hypophosphite hydrate, 8.1 g/L sodium citrate dihydrate, and 4.0 g/L ammonium chloride, at pH 9.25. About 5 mL of this nickel electroless bath was added to a small glass vial containing 200 zincated aluminium pins having a silver core. The vial was rotated at 75° C. for 15 minutes. The resulting substrates were nickel-plated, silver-cored aluminium pins.

Example 2

Electroless Deposition of Non-radioactive Palladium

The electroless deposition of 7 μg (micrograms) of non-radioactive palladium from different electroless baths onto 700 cleaned copper wires was evaluated. The results are summarized below:

| Bath Composition | % Bath Depletion[1] |
| --- | --- |
| 0.1 N HCl | 91.3% |
| Ammonium sulfate/citrate[2] | 0% |
| 0.001 N HCl | 97.3% |

[1] percent of Pd plated from the solution; and
[2] 13.2 g/L ammonium sulfate, 24.3 g/L ammonium citrate, and 50 mL/L ammonium hydroxide.

Example 3

Electroless Deposition of $^{103}$Pd

The electroless deposition of carrier-free $^{103}$Pd onto a nickel-coated substrate of Example 1 was carried out using an alkaline bath. The alkaline bath contained carrier-free $^{103}$Pd, ammonium hydroxide (50 mL/L), optional citrate (24.3 g/L) (as a buffer), and a hydrazine (12 mL/L) or a hypophosphite (4.1 g/L) (as a reducing agent). The tests showed a reproducible bath depletion of carrier-free $^{103}$Pd of over 90%.

It is apparent that many modifications and variations of the inventions as hereinabove set forth may be made without departing from the spirit and scope thereof. The specific embodiments described are given by way of example only, and the invention is limited only by the terms of the appended claims.

What is claimed is:

1. A brachytherapy seed which comprises:
   (a) a substrate having a surface suitable for the electroless deposition of palladium,
   (b) carrier-free $^{103}$Pd disposed on said surface of said substrate, wherein the $^{103}$Pd disposed on said surface of said substrate does not include non-radioactive palladium metal or other palladium isotopes added, or other non-radioactive metals, as a carrier, so as to provide a carrier-free $^{103}$Pd-laden substrate, wherein said surface is free of non-radioactive palladium and other metals; and
   (c) a biocompatible casing for encapsulating the carrier-free $^{103}$Pd-laden substrate.

2. The brachytherapy seed of claim 1, wherein the surface suitable for the electroless deposition of palladium is metallic.

3. The brachytherapy seed of claim 2, wherein the metallic surface comprises nickel, copper, or a mixture thereof.

4. The brachytherapy seed of claim 1, wherein the substrate further comprises a radiopaque metal.

5. The brachytherapy seed of claim 4, wherein the substrate comprises a radiopaque metal core surrounded by a sheath of a radiotransparent metal.

6. The brachytherapy seed of claim 5, wherein the radiopaque metal core comprises silver, gold, platinum, iridium, palladium, thallium, copper, iron or lead or a mixture thereof.

7. The brachytherapy seed of claim 5, wherein the radiotransparent metal comprises aluminium.

8. The brachytherapy seed of claim 7, wherein the radiopaque core comprises silver.

9. The brachytherapy seed of claim 1, wherein the substrate further comprises a radiotransparent core.

10. The brachytherapy seed of claim 9, wherein the radiotransparent core comprises graphite, a polymer, or a metal having a low atomic number.

11. The brachytherapy seed of claim 10, wherein the metal having a low atomic number is aluminium.

12. The brachytherapy seed of claim 1, wherein the biocompatible casing comprises stainless steel, titanium, a titanium alloy, tantalum, a nickel alloy, a copper alloy, or an aluminium alloy.

13. A method of treating a disease or condition responsive to brachytherapy, which comprises placing one or more brachytherapy seeds of claim 1 at a target location within an individual, and allowing the seeds to remain at the target location for a sufficient time to deliver a therapeutically effective radiation dose.

14. The method of claim 13, wherein the seeds are placed within the individual temporarily.

15. The method of claim 13, wherein the seeds are placed within the individual permanently.

16. The method of claim 13, wherein the disease or condition is selected from the group consisting of: head cancer, neck cancer, melanoma, brain cancer, non-small cell lung cancer, breast cancer, ovarian cancer, uterine cancer, cervical cancer, prostate cancer, liver cancer, proliferative disease, arthritis, urethral stricture, and fibroid uterine tumor.

17. A method of preparing a carrier-free $^{103}$Pd-laden substrate for a brachytherapy seed which comprises: immersing a substrate having a surface suitable for the electroless deposition of palladium into an electroless bath comprising carrier-free $^{103}$Pd for a sufficient time to deposit a pre-selected amount of carrier-free $^{103}$Pd onto the surface suitable for the electroless deposition of palladium of said substrate.

18. The method of claim 17, wherein the electroless bath further comprises an acid, a reducing agent, and optionally at least one of a complexing agent and a buffer.

19. The method of claim 17, wherein the electroless bath further comprises a base, a reducing agent, and optionally at least one of a complexing agent and a buffer.

* * * * *